United States Patent
Ettwein et al.

(10) Patent No.: US 11,369,396 B2
(45) Date of Patent: Jun. 28, 2022

(54) SURGICAL INSTRUMENT OF TWO-BRANCH DESIGN WITH IMPROVED CLEANING SUITABILITY

(71) Applicant: AESCULAP AG, Tuttlingen (DE)

(72) Inventors: Pierre Ettwein, Engen (DE); Robert Vogtherr, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 350 days.

(21) Appl. No.: 16/608,544

(22) PCT Filed: Apr. 27, 2018

(86) PCT No.: PCT/EP2018/060894
§ 371 (c)(1),
(2) Date: Oct. 25, 2019

(87) PCT Pub. No.: WO2018/197679
PCT Pub. Date: Nov. 1, 2018

(65) Prior Publication Data
US 2020/0197034 A1 Jun. 25, 2020

(30) Foreign Application Priority Data
Apr. 27, 2017 (DE) .......................... 102017109125.4

(51) Int. Cl.
*A61B 17/28* (2006.01)
*A61B 17/3201* (2006.01)
*A61B 90/00* (2016.01)

(52) U.S. Cl.
CPC ...... *A61B 17/2816* (2013.01); *A61B 17/3201* (2013.01); *A61B 2090/0813* (2016.02)

(58) Field of Classification Search
CPC ............ A61B 17/2816; A61B 17/3201; A61B 2090/0813; A61B 17/28; A61B 17/29;
(Continued)

(56) References Cited

U.S. PATENT DOCUMENTS

| 590,528 A | 9/1897 | Koch |
| 2005/0186536 A1 | 8/2005 | Zepf |
| 2012/0029554 A1 | 2/2012 | Kreidler |

FOREIGN PATENT DOCUMENTS

| CN | 202723937 U | 2/2013 |
| CN | 203436369 U | 2/2014 |

(Continued)

OTHER PUBLICATIONS

German Search Report for German Application No. 10 2017 109 125.4, with English translation, dated Feb. 14, 2018, 15 pages.

(Continued)

*Primary Examiner* — Kathleen S Holwerda
*Assistant Examiner* — Lauren Dubose
(74) *Attorney, Agent, or Firm* — Culhane Meadows, PLLC; Christopher A. Rothe (57) ABSTRACT

A medical-technical instrument includes a first instrument branch, a second instrument branch, and a bearing element coupling the instrument branches in a superimposed closure. The branches contact each other in a closure portion in an operation pivot region via mutually facing contact surfaces so that the branches in the operation pivot region contact each other with their respective contact surfaces, and the branches are positionable in a cleaning position outside the operation pivot region. The bearing element is fixed at an end portion on the first instrument branch and has a head widening conically in a continuous or stepped manner. The head penetrates a continuously or stepped conical passage opening in the second instrument branch. The passage opening is an elongated hole, and the bearing element is rotatably positionable in the elongated hole and translationally fixedly received.

16 Claims, 6 Drawing Sheets

(58) Field of Classification Search
CPC .... A61B 2017/2916; A61B 2017/2936; A61B 17/30; A61B 17/32; B26B 13/28; B26B 13/26; B26B 13/04; A01G 3/02; A01G 3/0255
USPC ......................................................... 606/159
See application file for complete search history.

(56) References Cited

FOREIGN PATENT DOCUMENTS

| | | | | |
|---|---|---|---|---|
| DE | 29712016 U1 | | 9/1997 | |
| DE | 20100589 U1 | | 5/2001 | |
| DE | 202004002560 U1 | | 4/2004 | |
| DE | 2594210 | * | 5/2013 | ............ A61B 17/28 |
| EP | 2412324 A2 | | 2/2012 | |
| EP | 2594210 A1 | | 5/2013 | |
| EP | 2873381 A1 | | 5/2015 | |
| JP | 2005204997 A | | 8/2005 | |

OTHER PUBLICATIONS

International Search Report and Written Opinion for International Application PCT/EP2018/060894, dated Jun. 18, 2018, 7 pages.

\* cited by examiner

SURGICAL INSTRUMENT OF TWO-BRANCH DESIGN WITH IMPROVED CLEANING SUITABILITY

CROSS REFERENCE TO RELATED APPLICATIONS

This application is the United States national phase entry of International Application No. PCT/EP2018/060894, filed Apr. 27, 2018, which claims the benefit of priority of German Application No. 10 2017 109 125.4, filed Apr. 27, 2017. The contents of International Application No. PCT/EP2018/060894 and German Application No. 10 2017 109 125.4 are incorporated by reference herein in their entireties.

FIELD

The invention relates to a scissor-like or forceps-like medical-technical instrument with a first instrument branch (instrument part) consisting of a distal engagement/operative portion, a proximal handle/holding portion, and an interposed coupling/closure portion, a second instrument branch (instrument part) also consisting of a distal engagement/operative portion, a proximal handle/holding portion, and an interposed coupling/closure portion, and a bearing element coupling the instrument branches (instrument parts) in a superimposed closure, whereby the two instrument branches (instrument parts) are pivotable relative to each other in a scissor-like manner and contact each other (slidingly) in the respective coupling/closure portions in an operation pivot region via mutually facing contact surfaces, so that the two instrument branches in the operation pivot region contact each other with their respective contact surfaces in a bearing and guiding manner (i.e. slidingly), and the instrument branches are positionable in a cleaning position outside the operation pivot region, wherein the bearing element is preferably threadless and is securely fixed at an end portion directly on the first instrument branch and has at the other end portion a head widening conically in a continuous or stepped manner with increasing distance from the first instrument branch, said head penetrating a continuously or stepped conical passage opening in the second instrument branch, wherein the passage opening is designed in the form of an elongated hole.

BACKGROUND

In known two-part medical-technical/surgical standard instruments of the scissor type and/or forceps type, on the one hand so-called superimposed closures and on the other hand so-called box locks are used as hinges between two instrument branches (instrument parts). Both versions have, inter alia, the disadvantage that there are covered gap surfaces in the hinge region between the pivotally coupled instrument branches, which are not exposed or accessible in any (angular) position of the branches due to the coupling of the instruments. Such covered gap surfaces do not allow optimal cleaning and sterilization of the instruments. In general, the branches of the instruments are brought into an open position of about 90° for cleaning, so that the covered surfaces are slightly reduced. An optimal cleaning result, however, is difficult to achieve even then.

There have been different approaches to reducing or eliminating the problem of insufficiently accessible or inaccessible gap surfaces between the branches of generic medical-technical instruments. For example, EP 2 594 210 A1 shows a scissor-like or forceps-like medical instrument with a first and a second branch (instrument part), which are pivotably connected by a bearing pivot with a radially widened head part on the one hand and a screw thread on the other hand. The first branch forms a guiding plate and the second branch forms a support plate into which the bearing pivot is screwed. The guiding plate has an aperture for the pivotable accommodation of the bearing pivot. The guiding plate and the support plate touch each other flatly in the normal operating state of the instrument. The aperture of the guiding plate is formed as an elongated hole (i.e. a penetrating longitudinal groove) extending in the longitudinal direction of the guiding plate, which has a first extended indentation in the edge region of its end region adjacent to the tool part and a second extended indentation in the edge region of its end region opposite in the longitudinal direction, in which the head part of the bearing pivot can optionally be accommodated. The first indentation has a smaller depth (T1) than the second indentation.

The support plate has on its contact surface facing the guiding plate a transverse groove (indentation) arranged in the area of the bearing pivot and running transversely to the support plate, the depth (T3) of which corresponds at least to the depth (T1) of the first indentation of the elongated hole and the width (b) of which corresponds at least to the width (B) of the guiding plate. The first branch can be brought with its guiding plate into a pivot position aligned with the transverse groove and can be adjusted in the transverse groove in the direction towards the bearing pivot to such an extent that the head part of the bearing pivot is disengaged from the first indentation of the elongated hole. The head part of the bearing pivot is to be brought into overlapping with the second indentation of the elongated hole by an adjustment of the second branch with its support plate and the bearing pivot along the elongated hole and is to be brought into engagement with the second indentation by an adjustment in the direction of the bearing pivot.

The guiding plate and the support plate are spaced apart in this position. With this instrument, the disadvantage is that the two branches have to be moved with respect to each other in a relatively complicated way for cleaning, whereby first the bearing pivot and the first indentation receiving it have to be disengaged. This may cause unwanted wear of the bearing. Moreover, due to the reduced countersinking depth for the screw head of the bearing pivot, the rotation guidance/the stability of the closure is limited, which can only be compensated for by a higher final thickness with corresponding disadvantages in the application, in particular the heaviness of the relative pivoting of the two branches. This solution therefore seems to be acceptable for scissors, but less suitable for more heavily loaded instruments such as forceps or the like.

EP 2 873 381 A1 discloses a medical instrument consisting of a first hand lever (instrument part) comprising a guiding plate and a second hand lever (instrument part) comprising a support plate, which are pivotably connected/coupled via a bearing pivot arranged in the region of the guiding plate and the support plate and provided with a radially widened head part. The support plate forms a respective receiving groove in its longitudinal edge regions, into which the guiding plate engages in its operating position. The support plate has an indentation between the receiving grooves that extends over the entire width of the support plate. The guiding plate can be rotated from its operating position to a cleaning position relative to the support plate, in which the guiding plate overlaps with the indentation on the support plate. In the area of the indentation, a spacer element is provided between the guiding plate and the support plate, the height of which in the direction of the bearing pivot is equal to or less than the depth of the indentation, so that the guiding plate cannot sink to the indentation base in the angular position covering the indentation.

The disadvantage of this instrument is that a visual inspection of the cleaning success in the closure gap in the cleaning position is only possible to a limited extent. In addition, the edge regions of the support plate form transitions or steps that can impair preparation (e.g. knots of suture material, trapping of tissue).

A similar instrument is known from EP 2 412 324 A2, in which a pivot pin protrudes through a second support plate and is provided with a radially widened annular flange in its end region protruding through the second support plate. This flange has a distance (a) from a first support plate which corresponds to twice the thickness (d) of the second support plate resting on the pivot pin or is greater than twice the thickness (d) of the second support plate, so that the second hand lever (instrument part) can be displaced in an open pivot position towards the first hand lever (instrument part) along the pivot pin into a position in which the opposing contact surfaces of the flattened support plates are exposed. However, the disadvantage of this instrument is that the pivot pin protrudes over the closure portion. Here, too, the edge regions of the support plate form transitions or steps that can affect preparation (e.g. knots of suture material, trapping of tissue).

DE 297 12 016 U1 discloses dismountable multi-purpose scissors in which the instrument parts are detachably coupled. From DE 20 2004 002 560 UI, dismountable dental forceps are also known. With these instruments, the dismountability of the instrument results in additional expenditure. In addition, when reassembling after cleaning, a correct pairing of instrument halves must be ensured. There is also a disadvantageous risk of confusion with different instrument sizes.

Finally, a surgical instrument is known from DE 201 00 589 U1 with two branches that are pivotably connected to each other and which have plane abutment surfaces that are adjacent to each other in the area of their pivot connection when the branches are pivoted in their working area.

Means are provided which, if the two branches are relatively shifted out of their working area, eliminate the flat contact of the abutment surfaces in certain sections. In the embodiment disclosed there with branches that can be moved into a cleaning position, the susceptibility to wear is disadvantageous, whereby there is also no/bad visibility into the closure portion for visual inspection of the cleaning success. In the embodiment with removable bearing pin, the assembly effort is also high and the bearing pin can also be lost. A visual inspection of the cleaning success in the closure gap in the cleaning position is only possible to a limited extent for a superimposed screw closure with cleaning gap. The screw connection as such may be disadvantageous with regard to cleaning suitability and/or corrosion resistance (inter alia, stress corrosion cracking).

Furthermore, there are instruments known in which a closure screw is screwed into one of the instrument branches up to contact with the stop (collar) and is slightly overtightened for securing, resulting in cold welding of the thread. The closure screw penetrates a stepped bore in the other instrument branch and has a screw head, which comes into contact with the other instrument branch and pushes/tensions it in the direction of the one instrument branch. The movement of the instrument (resulting from the tensioning of the instrument branches against each other) results from the distance between the abutment surface of the screw head to the contact surface of one instrument branch and the tolerances of the stepped bore of the other instrument branch. This overdetermines the screw connection. In practice, it is therefore often necessary to have closure screws of minimally different lengths available in order to compensate for manufacturing tolerances of the individual parts if required. This is linked with increased effort/costs. In addition, manual placement of the closure screws requires considerable experience in order to apply the optimum tightening torque. An automated, torque-controlled tightening of the connection screws is only possible to a limited extent due to the different influencing factors. In addition, instruments are known for which the closure screw is secured by a welding spot or by gluing in order to prevent loosening. A disadvantage may be in this case the lack of corrosion resistance resulting from the welding spot.

SUMMARY

The object underlying the invention is therefore to create a surgical instrument that at least partially eliminates the disadvantages described above, in particular to develop an instrument closure with good cleaning suitability that is also intuitively recognizable. In addition to easy cleanability, preferably a good visual inspection of the cleaning success should also be possible. The manufacturing effort and the manufacturing costs should preferably be as low as possible. Finally, the functionality of the instrument, in particular the smooth but precise guidance of the two branches (instrument parts) hinged together, should be guaranteed.

This object as well as the preferred goals are solved or achieved according to the invention by means of a (scissor-like or forceps-like) instrument, in particular by a scissor-like or forceps-like medical-technical instrument with a first instrument branch (instrument part) consisting of a distal engagement/operative portion, a proximal handle/holding portion, and an interposed coupling/closure portion, a second instrument branch (instrument part) also consisting of a distal engagement/operative portion, a proximal handle/holding portion, and an interposed coupling/closure portion, and a bearing element coupling the instrument branches (instrument parts) in a superimposed closure, whereby the two instrument branches (instrument parts) are pivotable relative to each other in a scissor-like manner and contact each other (slidingly) in the respective coupling/closure portions in an operation pivot region via mutually facing contact surfaces, so that the two instrument branches in the operation pivot region contact each other with their respective contact surfaces in a bearing and guiding manner (i.e. slidingly), and the instrument branches are positionable in a cleaning position outside the operation pivot region, wherein the bearing element is preferably threadless and is securely fixed at an end portion directly on the first instrument branch and has at the other end portion a head widening conically in a continuous or stepped manner with increasing distance from the first instrument branch, said head penetrating a continuously or stepped conical passage opening in the second instrument branch, wherein the passage opening is designed in the form of an elongated hole, wherein the bearing element is rotatably positionable in the elongated hole and translationally fixedly received, in particular fixedly received in position in the longitudinal direction of the elongated hole.

The bearing pivot is preferably threadless and is fixed to one branch in an integral or friction-locking manner, for example by riveting, welding, pressing and/or gluing. However, it may also have a thread. In this case, the screw connection can preferably be tightened by torque control. This results in a defined prestressing force between the branches. The screw connection can also be glued, welded or plastically deformed preferably by caulking.

The operation pivot region in the sense of the invention is understood to be a pivot region (pivot angle region) in which the two instrument branches are pivoted relative to each other when used as intended. This ensures that the two branches lie against each other (clearance-free) at their contact surfaces throughout the entire predetermined operation pivot region, and that the conical/(multiply) stepped head of the bearing element (bearing pivot/bearing bolt/bearing pin) and the conical/(multiply) stepped passage opening penetrated by it lie against each other (clearance-free) forming a kind of slide bearing, so that the branches are guided towards each other in the intended manner, i.e. in particular with the desired movement performance. In other words, in particular the (partially) conical shape of the bearing element head and the corresponding conical shape of the passage opening causes a force component to be generated in the longitudinal direction of the bearing element for slidably pressing the two instrument branches together and a force component to be generated perpendicular to the longitudinal direction of the bearing element, whereby bearing clearance in the radial direction of the bearing element is reduced/eliminated.

The cleaning position lies according to the invention outside the operation pivot region. In this cleaning position, the two instrument branches assume such a relative angular position to each other that the instrument according to the invention can be cleaned and (equally) sterilized particularly well and easily. Within the scope of the invention, the cleaning position can be located in a cleaning region in particular. The cleaning position is therefore not necessarily a concrete (angular) position of the two branches to each other, but rather a position/position area outside the operation pivot region in which the clearance or clearances provided according to a preferred embodiment of the invention lies/lie between the branches and preferably between the bearing-element head and the passage opening penetrated by it.

The branches of the instrument are preferably linked together in a so-called "superimposed closure". This means that the two instrument branches are preferably arranged on top of each other (not inside each other), so that one instrument branch rests on the other instrument branch (types 'superimposed', 'half-superimposed', and 'embedded' are also possible). In this preferred constellation, the two instrument branches are coupled by the bearing element. The bearing element defines a pivot axis around which the two instrument branches rotate relative to each other during pivoting. The coupling/closure portion is understood to be the portion of an instrument branch that is essentially completely covered by the other instrument branch when the instrument is completely closed, i.e. with an opening angle of 0° between the branches. The instrument branches are therefore preferentially placed over the closure portion and crossed (in the "superimposed" type also possible over the entire instrument length).

When and as long as the two instrument branches are positioned to each other in the operation pivot region, they lie (slidingly) against each other at their contact surfaces. In addition, the head of the bearing element contacts the inner walls of the passage opening (essentially) without clearance.

In the operation pivot region as well as in the cleaning position, according to the invention, the bearing element can be rotated or positioned to rotate in the passage opening, i.e. in the elongated hole, but it cannot be displaced translationally, i.e. it cannot be translationally relative positioned in the elongated hole in the direction of the longitudinal axis of the elongated hole.

The bearing element is designed and adapted to the two instrument branches in such a way that within the operation pivot region they are in sliding contact with each other and supported in the intended manner and with the intended movement performance (rotational resistance). According to the invention, the bearing element (bearing pin) is fixed to the first instrument branch. The position (axial position with respect to the longitudinal axis of the bearing element, aligned with the pivot axis) and inclination of the cone surface of its conical head is adapted to the position and inclination of the inner cone surface of the conical passage opening of the second instrument branch. It can be said that between the conical head of the bearing element and the inner conical surface of the second instrument branch in the direction of the pivot axis/longitudinal axis of the bearing element there is an (essentially) clearance-free fit, the strength of which determines the movement performance of the instrument. The stronger the two instrument branches are pressed or tensioned against each other by the cone surfaces of the bearing element and the passage opening in the second instrument branch, the greater the movement performance. Preferably, the two instrument branches are coupled to each other (essentially) without clearance by the bearing element in the operation pivot region. The conical outer surface of the bearing-element head and the conical inner surface of the passage opening of the second instrument branch form a kind of slide bearing and slide off each other when the instrument branches pivot towards each other.

The bearing element guides as a slide bearing only in the upper area (cone) and is preferably fixed in a threadless manner in the opposite first instrument branch, whereby of course a thread for fixing the bearing element is also conceivable. The above-mentioned disadvantages of the prior art can be avoided particularly well by the preferably threadless fixation. In particular, the joining and coupling of the two instrument branches together can be carried out automatically and force-controlled and/or, in the case of a thread, torque-controlled (torque-controlled screw connection), so that the invention offers the advantage that such an instrument no longer has to be joined manually. Any manufacturing tolerances can be compensated by, for example, force-controlled pressing in of a bearing element, e.g. in the form of a rivet, with simultaneous riveting. Moreover, the rivet head of such a rivet always acts with the same force (prestress) in the bearing position and the instrument closure always has the same gap or is identically clearance-free.

According to the invention, it is provided that the passage opening in the second instrument branch is formed as an elongated hole whose longitudinal axis extends in the longitudinal direction of the second instrument branch. Such a passage opening allows in the cleaning position in an advantageous way a reduction of the overlapping areas of both instrument branches to a minimum and thus a further improvement of the cleanability. Moreover, the more inaccessible portions of the branches in the closure portion can easily be visually inspected.

An embodiment of the invention may provide that the longitudinal axis of the elongated hole extends in the longitudinal direction (L) of the second instrument branch and, in particular, that the elongated hole extends in the width direction beyond both sides of the first instrument branch when the instrument branches are in the cleaning position.

The length of the elongated hole in the longitudinal direction (L) can in particular be greater than the width (B) of the first instrument branch. Alternatively or additionally, the length of the elongated hole in the longitudinal direction (L) can be greater than the length of the respective contact surfaces in the longitudinal direction (L).

One embodiment is characterized in that when pivoting the instrument branches (2, 3), the elongated hole (10) sweeps at least 90%, preferably 95% and more preferably 100% of the contact surface (15) of the first instrument branch (2).

According to one embodiment, the operation pivot region can extend from an opening angle between the instrument branches of 0° to an opening angle of between approx. 50° and 40°, preferably of approx. 45°. With an operation pivot region formed in this way, accidentally transferring the instrument from the operation pivot region to the cleaning position during use of the instrument can be prevented.

It is particularly advantageous if there is an opening angle between the instrument branches in the cleaning position of between approx. 50° and approx. 95°, preferably between 60° and 90°, particularly preferably of approx. 90°. This simplifies the transfer of the instrument from the operation pivot region to the cleaning position.

According to one embodiment, the bearing element can be formed as a bearing pin or bearing rivet, with an (essentially) cylindrical pin portion on the one hand and the adjacent, widening conical head on the other hand. Such a bearing element is particularly easy to fix on or in the first instrument branch. For example, the pin portion can be pressed into an opening, in particular a passage opening, of the first instrument branch. In particular, the pin portion can be force-locked to the first instrument branch, in particular pressed, riveted, plastically deformed or jammed. Alternatively or additionally, it can be connected to the instrument branch in an integral manner, in particular glued, soldered or welded. Finally, the bearing pin can also be screwed in and then optionally plastically deformed, glued or welded to prevent unintentional unscrewing of the screw connection.

One embodiment of the invention is characterized in that the elongated hole has a receiving portion whose width is expanded relative to the width A of the elongated hole, and the other end portion of the bearing element is rotationally positionably received in the receiving portion and has a diameter greater than the width A of the elongated hole. The receiving portion of the elongated hole may in particular be continuously conical or stepped conical.

The passage opening of the second instrument branch on the side facing the closure portion (on the side facing the first instrument branch) may in particular have an essentially cylindrical opening portion which has clearance with regard to the bearing element. In this way, jamming of the second instrument branch with the cone surface of the bearing element head can easily be prevented. Furthermore, it is also ensured that the cylindrical pin portion can be flushed/cleaned also within the passage opening. A special embodiment of the invention is characterized in that the cone angle (acute angle) lies between approx. 35° and approx. 55°, preferably between approx. 40° and 50°, in particular preferably at approx. 45°.

Figure 8:
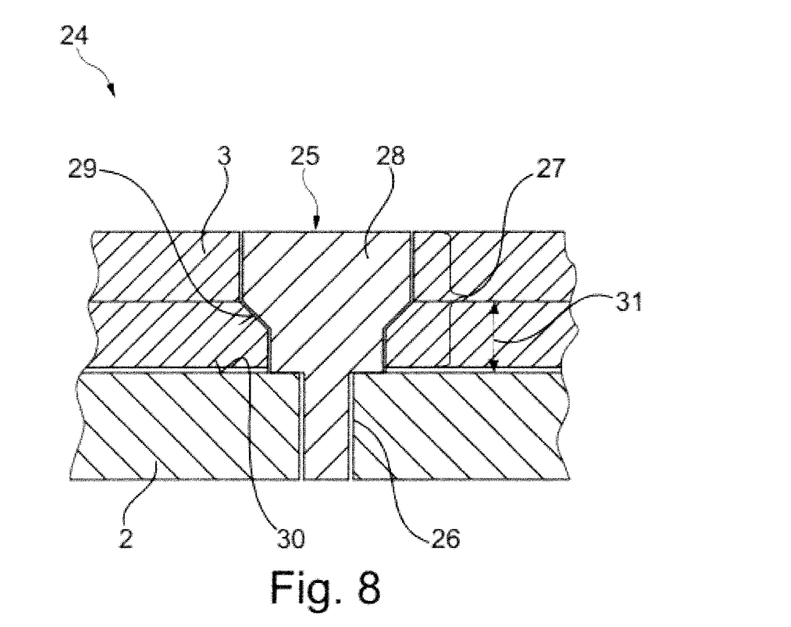
FIG. 8 shows a sectional view of a bearing screw screwed into an instrument according to the prior art.
Figure 9:
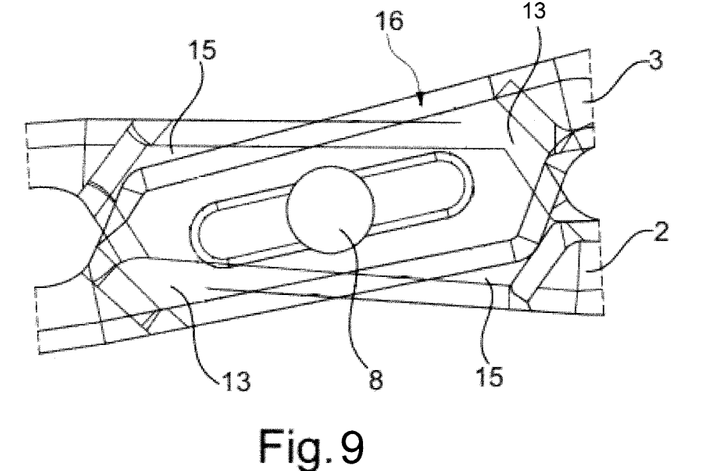
FIG. 9 shows an illustration corresponding to FIG. 3 of a further embodiment of the surgical instrument according to the invention without a groove in the branches.
Figure 10:
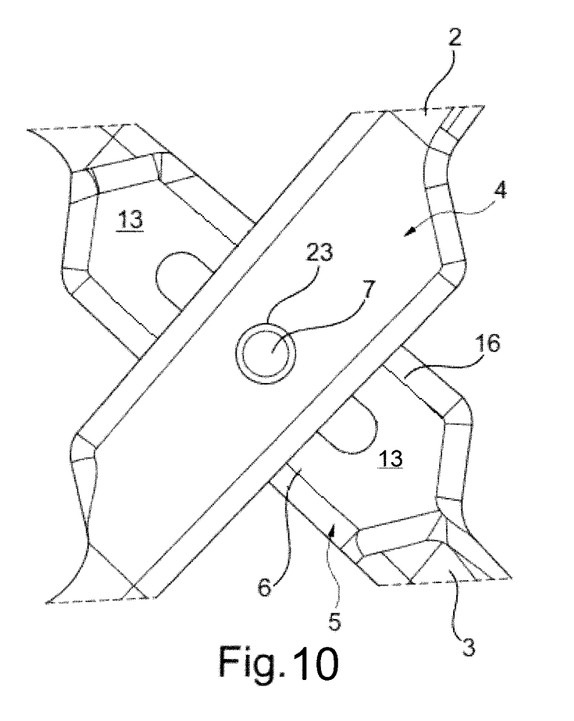
FIG. 10 shows the instrument according to the embodiment of FIG. 9 in a view from below.
Figure 11:
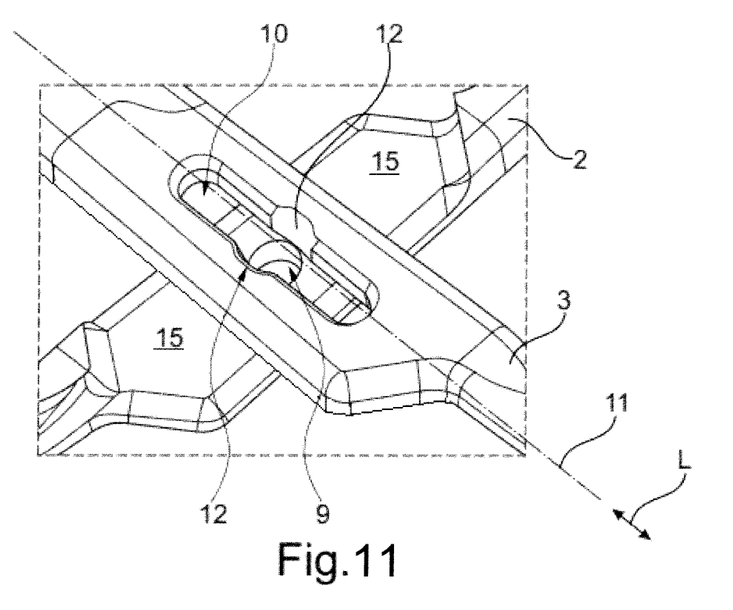
FIG. 11 shows a perspective view of the instrument according to the embodiment of FIGS. 9 and 10 in the position of FIG. 10 without bearing element.

Another embodiment is a cylindrical countersink with a conical outlet (see screw head FIG. 8). However, the connection element is not supported by a collar on the opposite instrument branch. Only the conical surfaces are used for bearing.

A further embodiment is characterized in that the closure portion of at least one of the instrument branches has a transverse groove and on both sides of the transverse groove a respective contact surface for the closure portion of the other instrument branch. A gap or clearance then exists between the instrument branches in a cleaning position outside the operation pivot region without mutual contact via the contact surfaces. The transverse groove (on one side, alternating sides, or both sides) (known from the prior art per se) is inserted into the coupling/closure portion in such a way that it is recessed in relation to opposed contact surfaces formed on the corresponding branch (instrument part) (on both sides) and the other branch (instrument part) can at least partially accommodate it in a cleaning (angular) position. The contact surfaces of both instrument branches are therefore designed in such a way that they essentially lie against each other without clearance throughout the entire operation pivot region (operation pivot-angle region) and, in particular, support each other with the desired movement performance (rotational resistance).

The transverse groove is incorporated in the closure portion of the at least one respective branch. It can be said that it is incorporated into the side or area of the at least one branch that faces the other branch. The transverse groove (in its groove width direction) is designed/measured in such a way that it at least partially accommodates the opposite instrument branch or its closure portion in the cleaning position (in the groove depth direction). Its width therefore corresponds to at least the width of the other opposite instrument branch in this region, i.e. in its closure portion and its groove depth corresponds at least partly to the thickness of the opposite branch. Preferably, the transverse groove has a width that is even slightly larger than the width of the other branch in the opposite closure portion, so that its (partial) accommodation in the transverse groove is ensured even if the instrument branches are only approximately positioned in the cleaning position.

When and as long as the two instrument branches are positioned relative to each other in the operation pivot region, there is a gap between the transverse groove bottom and the opposite instrument branch, the height of which (in the case of a transverse groove integrated in only one instrument branch) corresponds to the transverse groove depth. In the case of transverse grooves introduced into both instrument branches, the height of this gap corresponds to the sum of the two transverse groove depths. The transverse groove introduced into the at least one instrument branch does not affect the function of the instrument in the operation pivot region.

One embodiment of the invention may provide that the groove has a width (b) in the longitudinal direction of the respective instrument branch which is at least equal to the width (B) of the other instrument branch in its closure portion transverse to its longitudinal direction, wherein the width (b) of the groove is preferably slightly larger or larger than the width (B) of the branch. In this way, a simple and safe accommodation of the other instrument branch in the transverse groove can be ensured.

It is particularly advantageous if the groove has a depth of between approx. 1.0 mm to approx. 0.1 mm, preferably between approx. 0.7 mm to approx. 0.3 mm, especially preferably of approx. 0.5 mm. Such groove dimensions allow sufficient clearance between the instrument branches in the cleaning position for cleaning in the intended manner.

Another embodiment may furthermore provide that the two instrument branches are directly adjacent to each other, in particular without intermediate layers of further elements in the closure portion. In this way, the number of parts of the instrument can be kept small, which facilitates assembly.

Moreover, this ensures that the surfaces of the two instrument branches are actually spaced apart in the cleaning position and, in particular, are not covered by other components of the instrument between its branches, such as spacer springs or compression springs, which are intended to ensure that the branches are spaced apart.

It can also be said that according to the invention, a particularly good way of cleaning the closure portion is made possible without there having to be a gap between the instrument branches by incorporating the bearing element in the elongated hole so that it cannot be moved. In addition, a groove/transverse groove (indentation) can be used to create a gap in the closure portion on one or both of the inner end surfaces with a depth of at least 0.1 mm (previous experience, possibly less is also sufficient depending on the covered gap surface). The groove/transverse groove results in two positions of the instrument halves in relation to each other: up to approx. 45° opening angle (working area), the instrument halves are guided in the outer area, free of clearance, and can generate a movement resistance if required. Above approx. 45° opening angle (cleaning position), the groove/transverse groove is located under the opposite instrument half, resulting in clearance in the closure. This allows the closure portion and guide surfaces to be well rinsed, cleaned and sterilized. In addition, an elongated hole can be located in an instrument half, which enables good visual inspection of the cleaning in the closure portion. The elongated hole also improves the cleanability/rinsability of the closure. The connection element has a conical head, which is guided in a conical countersink on the upper side of the instrument half. The cone bearing between the bearing element and the one instrument half provides a rotation guide for a defined movement adjustment. Overall, the invention is an easy-to-clean instrument closure, which is intended to replace the previous closure (screw closure) and box lock and enables good visual inspection of the cleaning success in the closure portion. Preferably, a riveted connection can be used to implement a cost-effective and process-reliable connection solution.

The following advantages in particular can be achieved by the invention:
1) Better cleanability/rinsability of the region between the two instrument branches and better possibility of visual inspection of the cleaning success.
2) Simple and process-reliable adjustment of the 'movement' (rotational resistance) of the instrument branches by defined tensioning of the branches.
3) The fixed connection (e.g. riveted connection) enables cost-effective process automation, since there is no need for the complex placing of the connection screw, which has to be carried out manually according to the prior art. According to the invention, the bearing element can be fixed to one instrument half by the following fastening technologies: riveting, welding, pressing, gluing, plastically deforming.

Alternatively, a screwed connection can be used, which is not placed over the collar, but secured in the required position (welding, gluing, plastically deforming etc.).

BRIEF DESCRIPTION OF THE DRAWING FIGURES

The invention is explained in more detail below using drawings as examples. They show.

DETAILED DESCRIPTION

The drawings are only schematic in nature and serve only to understand the invention. The figures show two embodiments: FIGS. 1 to 7 relate to a first embodiment and FIGS. 1, 2, 6 and 9 to 11 relate to a second embodiment of the instrument according to the invention. As a comparison of FIG. 3 with 9 as well as 4 with 10 shows, the first and second embodiments differ in that a transverse groove 16 is formed in the first embodiment in the first instrument branch 2, while such a transverse groove is not present in the second embodiment. The following description applies to both the first and second embodiment, unless stated otherwise.

The scissor-type or forceps-type medical-technical instrument 1 shown as an example in the figures has a first instrument branch (instrument part) 2 and a second instrument branch (instrument part) 3 both in the first embodiment and in the second embodiment. The first instrument branch 2 has a first coupling/closure portion 4. The second instrument branch 3 has a second coupling/closure portion 5. The two instrument branches 2, 3 are coupled to each other in a so called superimposed closure, i.e. they are arranged on top of each other (not inside each other), so that the one, first instrument branch 2 lies on top of the other, second instrument branch 3 (on one side).

Figure 7:
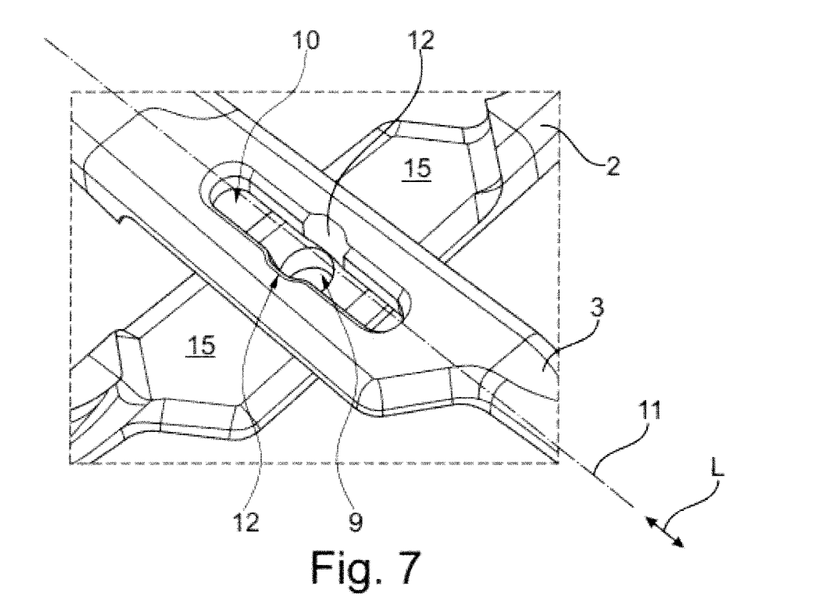
FIG. 7 shows a perspective view of the instrument in the position of FIGS. 2 and 4 without bearing element.

In this constellation, the two instrument branches 2, 3 are coupled to each other by a bearing element 6. The bearing element 6 is shown in a sectional view in FIGS. 5 and 6. It is designed as a bearing pin 6 and has an essentially cylindrical pin portion 7 on the one hand, and an axially expanding conical head 8 on its axial side opposite to the pin portion 7 on the other hand. According to the invention it is threadless and fixed with its pin portion 7 directly to the first instrument branch 2. For this purpose, the pin portion 7 is preferably inserted into a passage opening/bore 9 of the first instrument branch 2 as can be seen in FIG. 7. The pin portion 7 can be force-locked to the first instrument branch 2, e.g. pressed, riveted, plastically deformed or jammed, or can be integrally formed, in particular glued, soldered or welded. In the present embodiment example, it is pressed into the passage opening 9 and riveted at the end to the side facing away from the second instrument branch 3 and formed into a rivet head 23 (in addition to the conical head 8). There is a gap-free interference fit between the passage opening 9 and the pin portion 7.

A passage opening 10 in the second instrument branch 3 is formed as an elongated hole 10. Its longitudinal extension 11 extends in the longitudinal direction L of the second instrument branch 3. The passage opening 10 is conical, in such a way that it expands conically in a portion 12 with increasing distance from its side facing the first instrument branch 2. The conical portion 12 forms a receiving recess 12 corresponding to the shape of the head 8 of the bearing pin 6. The receiving recess 12 is not only conical, but also widened in a radial direction in relation to the width A of the elongated hole 10.

Figure 5:
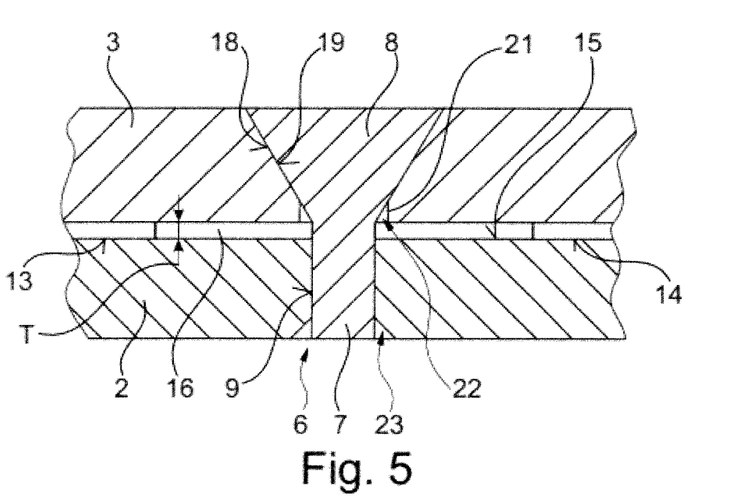
FIG. 5 shows a sectional view of the portion of FIG. 1 in the operation pivot region.
Figure 6:
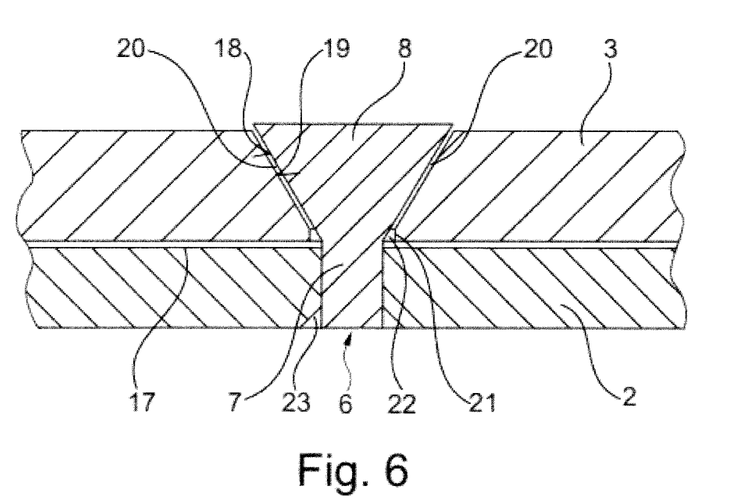
FIG. 6 shows a sectional view of the portion of FIG. 1 in the cleaning position.

The conical head 8 of the bearing element 6 widens with increasing distance from the first instrument branch 2 or respectively with increasing distance from the bearing pin 7. It penetrates the conically-widened passage opening 10 of the second instrument branch 3, which is easily recognizable in FIG. 7, and is in (flat) contact with the widened receiving recess 12. The conical outer surface 18 of the head 8 and the conical inner surface 19 of the receiving recess 12 form slide-bearing surfaces 18, 19 when pivoting the branches 2, 3 against each other or on each other. FIG. 5 shows that the elongated hole 10 has an essentially cylindrical opening portion 21 on its side facing the closure portion 5 (on the side facing the first instrument branch 2), which has a clearance 22 with respect to the bearing element 6 and its head 8.

The two instrument branches 2, 3 can be pivoted relative to each other due to their coupling by means of the bearing element 6.

In the first embodiment, the instrument branches 2, 3 contact each other in an operation pivot region via three contact surfaces 13, 14, 15 facing each other. In the second closure portion 5 of the second instrument branch 3, a first contact surface 13 and a second contact surface 14 are formed. In the first closure portion 4 of the first instrument branch 2, a third contact surface 15 is formed. Moreover, in the second closure portion 5 of the second instrument branch 3, the transverse groove 16 is formed such that a respective one of the contact surfaces 13, 14 is arranged on both sides of the transverse groove 16.

In the second embodiment, the instrument branches 2, 3 contact each other via two contact surfaces 13, 15 facing each other. In the second closure portion 5 of the second instrument branch 3, only the first contact surface 13 is formed. In the first closure portion 4 of the first instrument branch 2, the further contact surface 15 is formed. Furthermore, in the second closure portion 5 of the second instrument branch 3, unlike in the first embodiment, no transverse groove 16 is formed.

Figure 1:
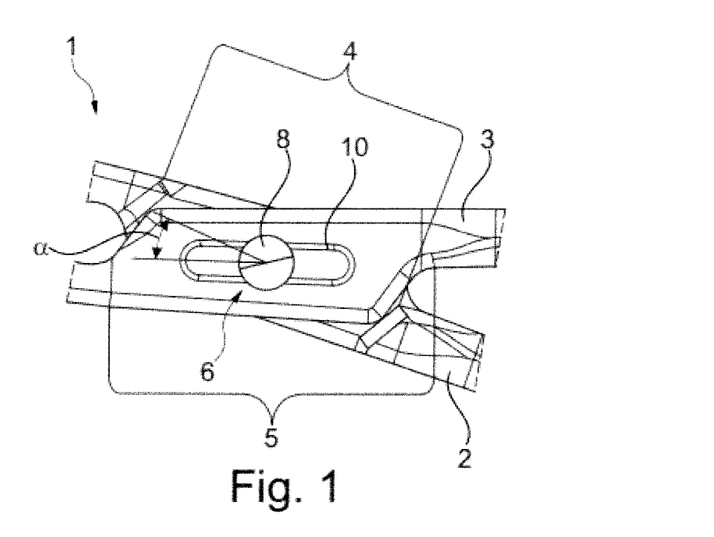
FIG. 1 shows a top view of a portion of a surgical instrument according to a first embodiment of the invention with a groove in one of the branches in a partially opened state in the operation pivot region.
Figure 2:
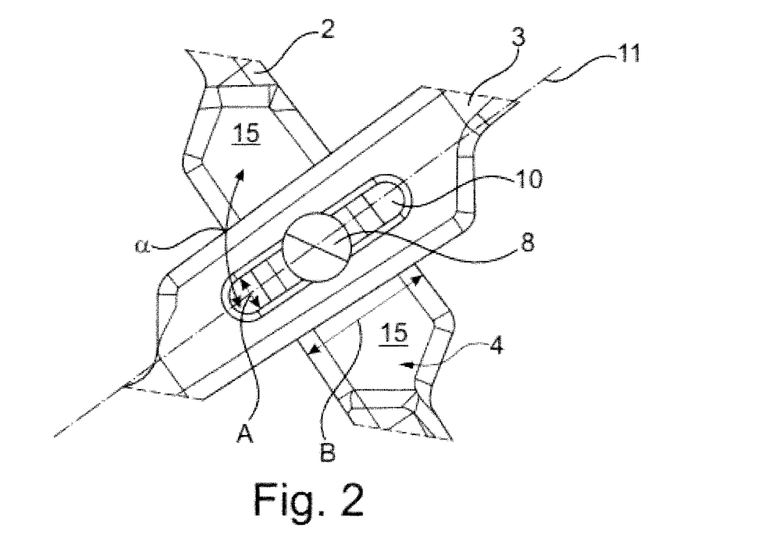
FIG. 2 shows a top view of the portion of the surgical instrument of FIG. 1 in an open state in the cleaning position]
Figure 3:
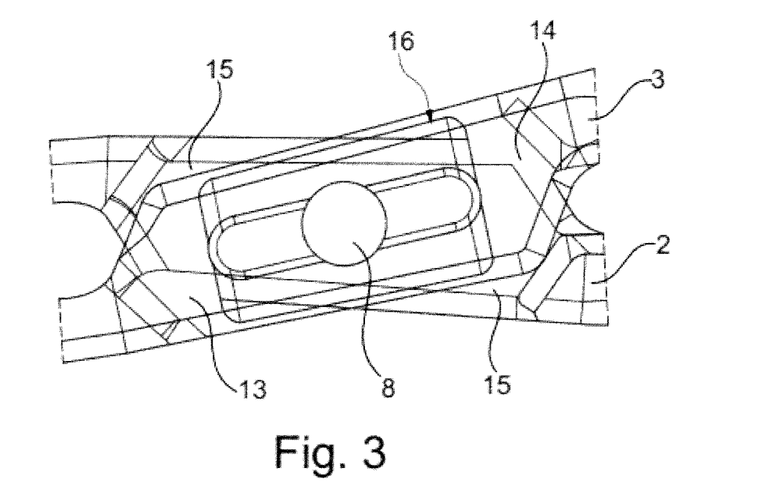
FIG. 3 shows the illustration of FIG. 1 with marked contact surfaces.
Figure 4:
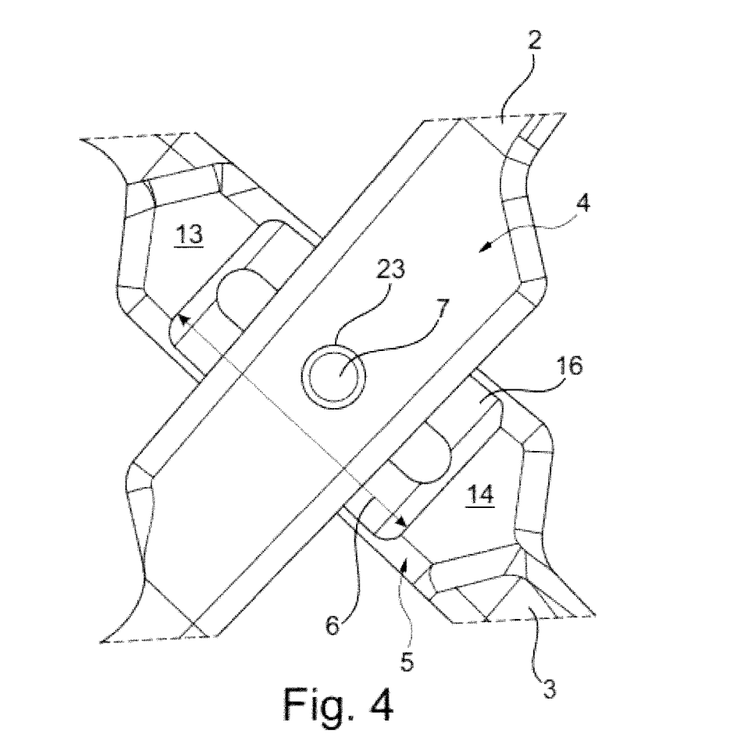
FIG. 4 shows the instrument in the position of FIG. 2 in a view from below.

In the first embodiment, the two instrument branches 2, 3 lie in an operation pivot region with their respective contact surfaces 13 and 14, respectively 15 in a bearing and guiding manner adjacent to each other. FIG. 3 indicates that the contact surfaces 13, 14 are shifted relative to the third contact surface 15 during pivoting of the two instrument branches 2, 3. As long as there is contact between the first contact surface 13 or the second contact surface 14 on the one hand, and the third contact surface 15 on the other hand, i.e. as long as these rest against each other, the two instruments are guided to each other and are located in the operation pivot region. If the contact surfaces 13, 14, 15 are separated from each other, the instrument 1 is no longer in the operation pivot region. The instrument 1 in the operation pivot region according to the first embodiment is shown in FIGS. 1, 3 and 5.

Outside the operation pivot region, the instrument 1 according to the first embodiment can be placed in a cleaning position. In this position there is a gap 17 or a clearance 17 between the instrument branches 2, 3 and in particular between their closure portions 4, 5 without contact to each other via the contact surfaces 13, 14, 15. Furthermore, there is a gap 20 or a clearance 20 between the slide-bearing surfaces 18, 19, i.e. between the head 8 of the bearing element 6 and the elongated hole 10, in particular the receiving recess 12. The instrument 1 in its cleaning position is shown in FIGS. 2, 4, 6 and 7.

The transverse groove 16 of the first embodiment has a width (b) in the longitudinal direction L of the second instrument branch 3 which is at least equal to the width (B) of the first instrument branch 2 in its closure portion 4 transverse to its longitudinal direction. In the present example, the width (b) of the transverse groove 16 is greater than the width (B) of the branch 2, see in particular FIG. 4. The transverse groove 16 has a depth T, see FIG. 5. The depth T of the transverse groove 16 is dimensioned in such a way that the gap 17 is formed and is present between the two closure portions 4, 5 of the instrument branches 2, 3 (and thus also between the contact surfaces 13, 14, 15) positioned in the cleaning position. In addition, the depth T of the transverse groove 16 and the receiving recess 12 in the elongated hole 10 are adapted to each other in such a way that the conical head 8 can detach itself from the receiving recess 12.

FIG. 8 shows a known instrument 24 in which a closure screw 25 is screwed into one of the instrument branches 2 up to contact with the stop (collar) and is slightly overtightened for securing, resulting in cold welding of the threads 26. The closure screw 25 penetrates a stepped bore 27 in the other instrument branch 3 and has a screw head 28 which comes into contact with the other instrument branch 3 and pushes/tensions it in the direction of the one instrument branch 2. The movement of the instrument 24 (resulting from the tensioning of the instrument branches 2, 3 against each other) results from the distance between the abutment surface 29 of the screw head 28 to the contact surface 30 of the one instrument branch 2 as well as the tolerances 31 of the stepped bore 27 of the other instrument branch 3. This overdetermines the screw connection.

In the second embodiment, the two instrument branches 2, 3 contact each other in an operation pivot region as well as in the cleaning position with their respective contact surfaces 13 or respectively 15, in a bearing and guiding manner.

The width of the head 8 is furthermore larger than the width A of the elongated hole 10, so that the bearing element 6 can be rotated in the receiving recess 12, but cannot be positioned translatorically in the elongated hole 10 in its longitudinal direction, i.e. it cannot escape from the receiving recess 12. Thus, in the second embodiment the two instrument branches 2, 3 are only (exclusively) rotatably coupled to each other. One possibility to clean the contact surfaces 13, 14, 15 is already the fact that the elongated hole 10 virtually sweeps them during pivoting of the instrument branches 2, 3 and that they are accessible for cleaning through the elongated hole 10.

The invention claimed is:

1. A medical-technical instrument comprising a first instrument branch, a second instrument branch, and a bearing element coupling the instrument branches in a superimposed closure, wherein the two instrument branches are pivotable relative to each other and contact each other in a closure portion in an operation pivot region via mutually facing contact surfaces,
so that the instrument branches in the operation pivot region contact each other with their respective contact surfaces in a bearing and guiding manner,
and the instrument branches are positionable in a cleaning position outside the operation pivot region,
wherein the bearing element is securely fixed at an end portion directly on the first instrument branch and has at the other end portion a head widening conically in a continuous or stepped manner with increasing distance from the first instrument branch, said head penetrating a continuously or stepped conical passage opening in the second instrument branch, wherein the continuously or stepped conical passage opening is an elongated hole, and
wherein the bearing element is rotatably positionable and translationally fixed in the elongated hole.

2. The medical-technical instrument according to claim 1, wherein the elongated hole has further a circular bulge or notch on a longitudinal flank of the elongated hole or in an opposite manner on both longitudinal flanks of the elongated hole, with which the bearing element is in engagement blocking a displacement along the elongated hole.

3. The medical-technical instrument according to claim 1, wherein the longitudinal axis of the elongated hole extends in a longitudinal direction of the second instrument branch when the instrument branches are in the cleaning position, in which the instrument branches are substantially at right angles to each other.

4. The medical-technical instrument according to claim 1, wherein a length of the elongated hole in the longitudinal direction is greater than a width of the first instrument branch and/or the length of the elongated hole in the longitudinal direction is greater than a length of the respective contact surfaces in the longitudinal direction.

5. The medical-technical instrument according to claim 1, wherein, when pivoting the instrument branches, the elongated hole sweeps at least 90% of the contact surface of the first instrument branch.

6. The medical-technical instrument according to claim 1, wherein the operation pivot region extends from an opening angle α between the instrument branches from 0° to approximately 50°, and/or between the instrument branches in the cleaning position there is an opening angle α of between approximately 50° and approximately 95°.

7. The medical-technical instrument according to claim 1, wherein the bearing element is designed as a bearing pin, having a cylindrical pin portion and the head, wherein the cylindrical pin portion is pressed into an opening of the first instrument branch.

8. The medical-technical instrument according to claim 7, wherein the cylindrical pin portion is force-lockingly connected to the first instrument branch, or is integrally connected.

9. The medical-technical instrument according to claim 2, wherein the circular bulge or notch forms a drill-shaped receiving portion, and a width of the drill-shaped receiving portion is widened in relation to a width of the elongated hole, and the other end portion of the bearing element is received in the drill-shaped receiving portion in a rotatably positionable manner and has a diameter which is greater than the width of the elongated hole.

10. The medical-technical instrument according to claim 9, wherein the drill-shaped receiving portion of the elongated hole is continuously conical or conically stepped.

11. The medical-technical instrument according to claim 1, wherein the continuously or stepped conical passage opening of the second instrument branch has, on the side facing the closure portion, a cylindrical opening portion which has a clearance with respect to the bearing element.

12. The medical-technical instrument according to claim 1, wherein the closure portion of each instrument branch has a transverse groove and has on both sides of the transverse groove the respective contact surface for the closure portion of the other instrument branch, wherein a gap or a clearance is present between the instrument branches in the cleaning position without contacting each other via the contact surfaces.

13. The medical-technical instrument according to claim 12, wherein the transverse groove has a width in a longitudinal direction of the first instrument branch which is at least equal to the width of the second instrument branch in its closure portion transversely to its longitudinal direction, wherein the width of the transverse groove is greater than the width of the second instrument branch and/or the transverse groove has a depth of between approximately 1.0 mm to approximately 0.1 mm.

14. A medical-technical instrument comprising a first instrument branch, a second instrument branch, and a bearing element coupling the instrument branches in a superimposed closure,
wherein the two instrument branches are pivotable relative to each other and contact each other in a closure portion in an operation pivot region via mutually facing contact surfaces,
so that the instrument branches in the operation pivot region contact each other with their respective contact surfaces in a bearing and guiding manner,
and the instrument branches are positionable in a cleaning position outside the operation pivot region,
wherein the bearing element is securely fixed at an end portion directly on the first instrument branch and has at the other end portion a head widening conically in a continuous or stepped manner with increasing distance from the first instrument branch, said head penetrating a continuously or stepped conical passage opening in the second instrument branch, wherein the continuously or stepped conical passage opening is designed in the form of an elongated hole, and
wherein the continuously or stepped conical passage opening consists of exactly one receiving portion corresponding to the head and widened in relation to a width of the continuously or stepped conical passage opening for translationally fixing the head of the bearing element in the receiving portion.

15. The medical-technical instrument according to claim 14, wherein the bearing element is fixed in a middle portion of the elongated hole with respect to a longitudinal direction of the elongated hole, such that the elongated hole extends on both sides of the bearing element.

16. The medical-technical instrument according to claim 1, wherein the bearing element is fixed in a middle portion of the elongated hole with respect to a longitudinal direction of the elongated hole, such that the elongated hole extends on both sides of the bearing element.

* * * * *